(12) United States Patent
Dunning et al.

(10) Patent No.: US 10,828,102 B2
(45) Date of Patent: Nov. 10, 2020

(54) ABLATION PROBE WITH TISSUE SENSING CONFIGURATION

(71) Applicant: Covidien LP, Mansfield, MA (US)

(72) Inventors: James E. Dunning, Lafayette, CO (US); Eric W. Larson, Littleton, CO (US); Jennifer McHenry, Denver, CO (US)

(73) Assignee: Covidien LP, Mansfield, MA (US)

( * ) Notice: Subject to any disclaimer, the term of this patent is extended or adjusted under 35 U.S.C. 154(b) by 161 days.

(21) Appl. No.: 15/905,065

(22) Filed: Feb. 26, 2018

(65) Prior Publication Data

US 2018/0235696 A1 Aug. 23, 2018

Related U.S. Application Data

(62) Division of application No. 14/064,472, filed on Oct. 28, 2013, now Pat. No. 9,901,399.

(Continued)

(51) Int. Cl.
*A61B 18/18* (2006.01)
*B23K 26/361* (2014.01)
(Continued)

(52) U.S. Cl.
CPC ........ *A61B 18/1815* (2013.01); *B23K 26/361* (2015.10); *B23K 26/362* (2013.01);
(Continued)

(58) Field of Classification Search
CPC ........ A61B 18/1815; A61B 2018/1869; A61B 2018/00023; A61B 2018/00875; A61B 2018/00577
See application file for complete search history.

(56) References Cited

U.S. PATENT DOCUMENTS

| D223,367 S | 4/1972 | Kountz |
| 4,291,708 A | 9/1981 | Frei et al. |

(Continued)

FOREIGN PATENT DOCUMENTS

| CN | 1103807 C | 3/2003 |
| DE | 390937 C | 3/1924 |

(Continued)

OTHER PUBLICATIONS

Mouser Electronics. Spring-loaded pins datasheet. Retrieved on Jan. 20, 2016 from http://www.mouser.com/ProductDetail/Mill-Max/0906-0-15-20-76-14-11-0/?qs=sGAEpiMZZMu2RFV024JNk1ZV1gAkUw03A0T%2fFU81DTc%3d.

(Continued)

*Primary Examiner* — Jason L Vaughan
*Assistant Examiner* — Amanda Kreiling

(57) ABSTRACT

An ablation probe is provided. The ablation probe includes a housing that is configured to couple to a microwave energy source. A shaft extends distally from the housing and includes a radiating section at a distal end thereof. A sensor assembly is operably disposed on the housing and includes a pair of sensor contacts. One or more sensors are positioned adjacent the radiating section and extend along the shaft. The sensor(s) have a pair of sensor contact pads that are positioned on the shaft for contact with the pair of sensors such that during transmission of microwave from the radiating section into target tissue at least one electrical parameter is induced into the at least one sensor and detected by the pair of sensor contacts.

17 Claims, 8 Drawing Sheets

Related U.S. Application Data

(60) Provisional application No. 61/738,021, filed on Dec. 17, 2012.

(51) Int. Cl.
    *B23K 26/362*     (2014.01)
    *H05B 6/64*     (2006.01)
    *H01R 4/60*     (2006.01)
    *A61B 18/00*     (2006.01)
    *A61B 17/00*     (2006.01)

(52) U.S. Cl.
    CPC ......... *H05B 6/6408* (2013.01); *H05B 6/6447* (2013.01); *A61B 2017/00526* (2013.01); *A61B 2018/00023* (2013.01); *A61B 2018/00577* (2013.01); *A61B 2018/00875* (2013.01); *A61B 2018/1869* (2013.01); *A61B 2562/225* (2013.01); *A61B 2562/227* (2013.01); *H01R 4/60* (2013.01); *Y10T 29/49117* (2015.01)

(56) References Cited

U.S. PATENT DOCUMENTS

| | | |
|---|---|---|
| D263,020 S | 2/1982 | Rau, III |
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |
| D354,218 S | 1/1995 | Van de Peer |
| 5,423,810 A | 6/1995 | Goble et al. |
| 5,500,012 A | 3/1996 | Brucker et al. |
| 5,810,804 A | 9/1998 | Gough et al. |
| D424,693 S | 5/2000 | Pruter |
| D424,694 S | 5/2000 | Tetzlaff et al. |
| D425,201 S | 5/2000 | Tetzlaff et al. |
| 6,059,780 A | 5/2000 | Gough et al. |
| 6,123,702 A | 9/2000 | Swanson et al. |
| D449,886 S | 10/2001 | Tetzlaff et al. |
| D457,958 S | 5/2002 | Dycus et al. |
| D457,959 S | 5/2002 | Tetzlaff et al. |
| 6,494,882 B1 | 12/2002 | Lebouitz et al. |
| 6,500,175 B1 | 12/2002 | Gough et al. |
| 6,569,162 B2 | 5/2003 | He |
| D487,039 S | 2/2004 | Webster et al. |
| 6,702,810 B2 | 3/2004 | McClurken et al. |
| 6,706,040 B2 | 3/2004 | Mahon et al. |
| D496,997 S | 10/2004 | Dycus et al. |
| D499,181 S | 11/2004 | Dycus et al. |
| 6,962,587 B2 | 11/2005 | Johnson et al. |
| 7,025,765 B2 | 4/2006 | Balbierz et al. |
| D525,361 S | 7/2006 | Hushka |
| 7,108,696 B2 | 9/2006 | Daniel et al. |
| D531,311 S | 10/2006 | Guerra et al. |
| D533,942 S | 12/2006 | Kerr et al. |
| D535,027 S | 1/2007 | James et al. |
| 7,160,296 B2 | 1/2007 | Pearson et al. |
| D541,418 S | 4/2007 | Schechter et al. |
| D541,938 S | 5/2007 | Kerr et al. |
| D564,662 S | 3/2008 | Moses et al. |
| 7,344,533 B2 | 3/2008 | Pearson et al. |
| D576,932 S | 9/2008 | Strehler |
| 7,419,487 B2 | 9/2008 | Johnson et al. |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| D634,010 S | 3/2011 | DeCarlo |
| 8,257,349 B2 | 9/2012 | Orszulak |
| D681,810 S | 5/2013 | DeCarlo |
| 8,655,454 B2 | 2/2014 | Prakash et al. |
| 8,795,268 B2 | 8/2014 | Willyard |
| 8,852,180 B2 | 10/2014 | Brannan |
| 8,906,008 B2 | 12/2014 | Brannan et al. |
| 8,920,410 B2 | 12/2014 | Brannan |
| 8,945,113 B2 | 2/2015 | Brannan et al. |
| 8,968,290 B2 | 3/2015 | Brannan et al. |
| 8,968,300 B2 | 3/2015 | Brannan |
| 9,017,328 B2 | 4/2015 | Bahney |
| 9,066,681 B2 | 6/2015 | Arts et al. |
| 9,168,178 B2 | 10/2015 | Reid, Jr. et al. |
| 9,192,308 B2 | 11/2015 | Brannan et al. |
| 9,192,426 B2 | 11/2015 | Brannan et al. |
| 9,192,439 B2 | 11/2015 | Dunning et al. |
| 9,192,440 B2 | 11/2015 | Rossetto |
| 9,332,959 B2 | 5/2016 | Arts et al. |
| 9,358,067 B2 | 6/2016 | Lee et al. |
| 9,364,278 B2 | 6/2016 | DeCarlo et al. |
| 9,370,392 B2 | 6/2016 | Sharonov |
| 9,375,196 B2 | 6/2016 | Zheng |
| 9,396,645 B2 | 7/2016 | Will |
| 9,439,712 B2 | 9/2016 | Sharonov |
| 9,504,524 B2 | 11/2016 | Behnke, II |
| 9,522,033 B2 | 12/2016 | Brannan |
| 9,526,568 B2 | 12/2016 | Ohri et al. |
| 9,649,146 B2 | 5/2017 | Orszulak |
| 9,668,802 B2 | 6/2017 | Brannan |
| 9,814,844 B2 | 11/2017 | Ohri et al. |
| 9,833,286 B2 | 12/2017 | Podhajsky |
| 9,901,398 B2 | 2/2018 | Brannan et al. |
| 9,901,399 B2 | 2/2018 | Dunning et al. |
| 2002/0077627 A1 | 6/2002 | Johnson et al. |
| 2002/0120261 A1 | 8/2002 | Morris et al. |
| 2003/0199863 A1 | 10/2003 | Swanson et al. |
| 2004/0097805 A1 | 5/2004 | Verard et al. |
| 2005/0137662 A1 | 6/2005 | Morris et al. |
| 2006/0163744 A1 | 7/2006 | Vanheusden et al. |
| 2007/0173806 A1 | 7/2007 | Orszulak et al. |
| 2007/0203551 A1 | 8/2007 | Cronin et al. |
| 2008/0125775 A1 | 5/2008 | Morris |
| 2008/0281314 A1 | 11/2008 | Johnson et al. |
| 2008/0287944 A1 | 11/2008 | Pearson et al. |
| 2009/0187180 A1 | 7/2009 | Brannan |
| 2009/0240273 A1 | 9/2009 | DeCarlo |
| 2009/0306655 A1* | 12/2009 | Stangenes ............ A61B 5/0422 606/41 |
| 2010/0114086 A1 | 5/2010 | Deem et al. |
| 2010/0217253 A1 | 8/2010 | Mehta |
| 2011/0092972 A1 | 4/2011 | Allen |
| 2011/0118724 A1 | 5/2011 | Turner et al. |
| 2011/0152853 A1 | 6/2011 | Manley et al. |
| 2011/0184403 A1 | 7/2011 | Brannan |
| 2011/0190754 A1 | 8/2011 | Kim et al. |
| 2011/0208184 A1 | 8/2011 | Brannan |
| 2011/0223812 A1* | 9/2011 | Prest .................... H01R 13/035 439/669 |
| 2012/0010505 A1 | 1/2012 | Allen |
| 2012/0010604 A1 | 1/2012 | Allen |
| 2012/0116388 A1 | 5/2012 | Houser et al. |
| 2013/0317495 A1 | 11/2013 | Brannan |
| 2013/0324910 A1 | 12/2013 | Ohri et al. |
| 2013/0324911 A1 | 12/2013 | Ohri et al. |
| 2013/0345541 A1 | 12/2013 | Nau, Jr. |
| 2013/0345552 A1 | 12/2013 | Arts et al. |
| 2014/0018793 A1 | 1/2014 | Sharonov |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |

(56) References Cited

FOREIGN PATENT DOCUMENTS

| | | |
|---|---|---|
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 246350 A1 | 11/1987 |
| EP | 0521264 A2 | 1/1993 |
| EP | 556705 A1 | 8/1993 |
| EP | 0558429 A1 | 9/1993 |
| EP | 0648515 A1 | 4/1995 |
| EP | 836868 A2 | 4/1998 |
| EP | 882955 A1 | 12/1998 |
| EP | 1159926 A2 | 3/2003 |
| EP | 1810628 A1 | 7/2007 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 55106 | 1/1993 |
| JP | 0540112 | 2/1993 |
| JP | 06343644 A | 12/1994 |
| JP | 07265328 A | 10/1995 |
| JP | 08056955 | 3/1996 |
| JP | 08252263 A | 10/1996 |
| JP | 09000492 A | 1/1997 |
| JP | 09010223 | 1/1997 |
| JP | 11244298 A | 9/1999 |
| JP | 2000342599 A | 12/2000 |
| JP | 2000350732 A2 | 12/2000 |
| JP | 20018944 | 1/2001 |
| JP | 2001003776 A | 1/2001 |
| JP | 200129356 | 2/2001 |
| JP | 200137775 A | 2/2001 |
| JP | 2001128990 A | 5/2001 |
| JP | 2001231870 A | 8/2001 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 1/1965 |
| SU | 401367 A1 | 10/1973 |
| SU | 727201 A2 | 4/1980 |
| WO | 0036985 A2 | 6/2000 |
| WO | 0174252 A2 | 10/2001 |
| WO | 2006105121 A2 | 10/2006 |
| WO | 2007/100559 A2 | 9/2007 |
| WO | 2010035831 A1 | 4/2010 |

OTHER PUBLICATIONS

LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May-Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page; Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform": Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W, "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001 pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure. "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).

(56) References Cited

OTHER PUBLICATIONS

Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 110-415, 1997.
T.Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis.TM. Technology (Date Unknown). "Overcoming the Challenge" located at: <(http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—COA-COMP" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993, Roger A. Stern.
U.S. Appl. No. 08/483,742, filed Jun. 7, 1995, Roger A. Stern.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.

Anonymous. (1987) Homer Mammalok. TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division. (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology. vol. 102, No. 1, Jul. 2003.
B. Levy M.D. et al., "Update on Hysterectomy New Technologies and Techniques" OBG Management. Feb. 2003.
B. Levy M.D.. "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1, (Jul. 1991) pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al.. "Antennas for Medical Applications", Antenna Handbook: Theory Application and Design, p. 24-40. Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure. TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52. No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions", In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone", Neurosurgery 15:(1984) pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al. "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts". Nov. 1, 2003; 4 pages.
Geddes et al., "The Measurement of Physiologic Events by Electrical Impedance" Am. J. MI, Jan. Mar. 1964, pp. 16-27.

(56) References Cited

OTHER PUBLICATIONS

Goldberg et al., "Image-guided Radiofrequency Tumor Ablation: Challenges and Opportunities—Part I", (2001) J Vasc. Interv. Radiol, vol. 12, pp. 1021-1032.

Goldberg et al. (1995) "Saline-enhanced RF Ablation: Demonstration of Efficacy and Optimization of Parameters", Radiology, 197(P): 140 (Abstr).

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure. TM. Vessel Sealing System: A Case Report" Innovations That Work, Feb. 2002.

Humphries Jr. et al., "Finite-Element Codes to Model Electrical Heating and Non-Linear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands. vol. 4; No. 1. pp. 307-320.

Jarrett et al., "Use of the LigaSure.TM. Vessel Sealing System for Peri-Hilar Vessels in Laparoscopic Nephrectomy" Sales/Product Literature 2000.

Johnson et al. "Evaluation of a Bipolar Electrothermal Vessel Sealing Device in Hemorrhoidectomy" Sales/Product Literature; Jan. 2004.

Johnson, "Evaluation of the LigaSure.TM. Vessel Sealing System in Hemorrhoidectormy" American College of Surgeons (ACS) Clinic La Congress Poster (2000).

Johnson et al., "New Low-Profile Applicators for Local Heating of Tissues", IEEE Transactions on Biomedical Engineering, vol. BME-31, No. 1, Jan. 1984, pp. 28-37.

Johnson, "Use of the LigaSure.TM. Vessel Sealing System in Bloodless Hemorrhoidectomy" Innovations That Work, Mar. 2000.

Joseph G. Andriole, M.D., et al., "Biopsy Needle Characteristics Assessed in the Laboratory", Radiology 148: 659-662, Sep. 1983.

Joseph Ortenberg, "LigaSure.TM. System Used in Laparoscopic 1st and 2nd Stage Orchiopexy" Innovations That Work, Nov. 2002.

Kennedy et al. "High-burst-strength, feedback-controlled bipolar vessel sealing" Surgical Endoscopy (1998) 12:876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

\* cited by examiner

ABLATION PROBE WITH TISSUE SENSING CONFIGURATION

CROSS REFERENCE TO RELATED APPLICATIONS

The present application is a divisional application of U.S. patent application Ser. No. 14/064,472 filed on Oct. 28, 2013, now U.S. Pat. No. 9,901,399, which claims priority to U.S. Provisional Application Ser. No. 61/738,021, filed on Dec. 17, 2012, the entire contents of each of which are incorporated herein by reference.

BACKGROUND

Technical Field

The present disclosure relates to an ablation probe. More particularly, the present disclosure relates to an ablation probe with one or more tissue sensing configurations.

Description of Related Art

Utilizing microwave thermal therapy to treat target tissue is known in the art. Specifically, one or more suitable microwave antennas that are coupled to an energy source may be positioned adjacent target tissue. Subsequently, electrosurgical energy, e.g., microwave energy, may be transmitted to a radiating section of the microwave antenna and is directed to target tissue, which, in turn, results in thermal coagulation. Typically, a surgeon relies on one or more imaging devices, systems and/or techniques to facilitate in the microwave thermal therapy. For example, such imaging devices, systems and/or techniques may be utilized to determine placement of the microwave antenna relative to target tissue, ablation completion of target tissue and/or ablation zone size of treated target tissue.

While the aforementioned imaging devices, systems and/or techniques may work well in a number of applications, (e.g., determining, for example, placement of the microwave antenna relative to target tissue) such imaging devices, systems and/or techniques, typically, do not provide automatic shut off when the microwave antenna is purposefully and/or inadvertently withdrawn from or not fully inserted into target tissue. In either of the foregoing scenarios, unintentional thermal injury to a patient and/or clinician is possible.

SUMMARY

As can be appreciated, an ablation probe with one or more tissue sensing configurations may prove useful in the surgical arena. Specifically, one or more tissue sensing configurations that are configured to detect ablation probe placement within tissue can prove advantageous for increasing performance and/or patient safety.

Embodiments of the present disclosure are described in detail with reference to the drawing figures wherein like reference numerals identify similar or identical elements. As used herein, the term "distal" refers to the portion of a surgical instrument that is being described which is further from a user, while the term "proximal" refers to the portion of the surgical instrument that is being described which is closer to a user.

An aspect of the present disclosure provides an ablation probe. The ablation probe includes a housing that is configured to couple to a microwave energy source. A shaft extends distally from the housing and includes a radiating section at a distal end thereof. A sensor assembly is operably disposed within the housing and includes a pair of sensor contacts. One or more sensors are positioned adjacent the radiating section and extend along the shaft. The sensor(s) have a pair of sensor contact pads that are positioned on the shaft for contact with the pair of sensors. During transmission of microwave energy from the radiating section into target tissue one or more electrical parameters are induced into the sensor(s) and detected by the pair of sensor contacts. The electrical parameter(s) may be impedance and/or capacitance. The electrical parameter(s) may be induced via an interrogatory pulse generated from a circuit of the microwave energy source.

The sensor(s) and the pair of sensor contact pads may be formed from a silver ink deposition that is provided on an exterior surface of the shaft. The silver ink deposition may be provided on the exterior surface of the shaft via pad printing, laser ablation and/or direct write. The silver ink deposition may include two or more depositions that are spaced-apart from one another forming two or more conductive traces that culminate at the sensor contact pads.

Moreover, the sensor assembly may include a sensor housing that is configured to support the pair of sensor contacts. The sensor contacts of the pair of sensor contacts may be positioned apart from one another within the sensor housing to contact the sensor contact pads and may include a proximal end and distal end. The distal ends may be disposed in oblique relation with respect to the proximal ends. Each sensor contact of the pair of sensor contacts may be resilient and configured to flex when the shaft is inserted through an aperture in the sensor housing for coupling to the housing. Each sensor contact of the pair of sensor contacts may be configured to couple to a corresponding lead that extends within the housing and couples to the microwave energy source for communication with one or more modules associated therewith. The proximal ends of the sensors may be configured to couple to corresponding clocking features that are provided on an end cap and hub that are positioned within the housing. The clocking features may be configured to facilitate aligning and coupling the sensor housing to the housing of the ablation probe.

The radiating section may be configured to transmit microwave energy at a frequency that ranges from about 2300 MHz to about 2450 MHz. Moreover, a polyester heat shrink wrap may be provided along the shaft and covers the sensor(s). Additionally, a ceramic trocar tip may be provided at distal tip of the shaft and may be configured to pierce tissue. Further, in-flow and out-flow tubes may be provided on the housing of the ablation probe and configured to cool the radiating section of the shaft.

An aspect of the present disclosure provides a method for manufacturing a microwave ablation probe. A housing configured to couple to a microwave energy source is formed. A shaft having a radiation section and one or more sensors including a pair of sensor contacts is formed. A sensor assembly including a sensor housing that couples to a pair of sensor contacts is formed. The shaft is coupled to the housing such that each sensor of the pair of sensors contacts a corresponding one of the sensor contacts such that during transmission of microwave energy from the radiating section into target tissue one or more electrical parameters may be induced into the sensor(s) and detected by the pair of sensor contacts.

The method may include forming the sensor(s) including the pair of sensor contact pads via a silver ink deposition that is provided on an exterior surface of the shaft. The method may include utilizing a process such as, for example, pad printing, laser ablation and direct write to provide the silver ink deposition on the exterior surface of the shaft.

Forming the sensor(s) including the pair of sensor contact pads via a silver ink deposition may include forming two or more depositions that are spaced-apart from one another forming at least two conductive traces that culminate at the sensor contact pads.

The method may include utilizing an overmolding process to couple the sensor housing to the pair of sensor contacts. The method may also include bending each sensor contact of the pair of sensor contacts such that the sensor contacts are angled toward one another and are positioned apart from one another within the sensor housing to contact the sensor contact pads.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In accordance with the instant disclosure, one or more sensor configurations are provided on an ablation probe to detect one or more properties that may be associated with target tissue and/or a specific surgical procedure. Specifically, the sensor configuration(s) provides feedback to a clinician or directly to a source of electrosurgical energy, e.g., a microwave generator, to improve overall performance of the ablation device and/or safety to a patient or clinician. To this end, the sensor configuration(s) includes one or more conductive traces that are deposited on an exterior surface of a shaft of the ablation probe and interrogated at a predetermined frequency to measure one or more electrical properties, e.g., capacitance and/or impedance, that are induced in the conductive traces.

Figure 1:
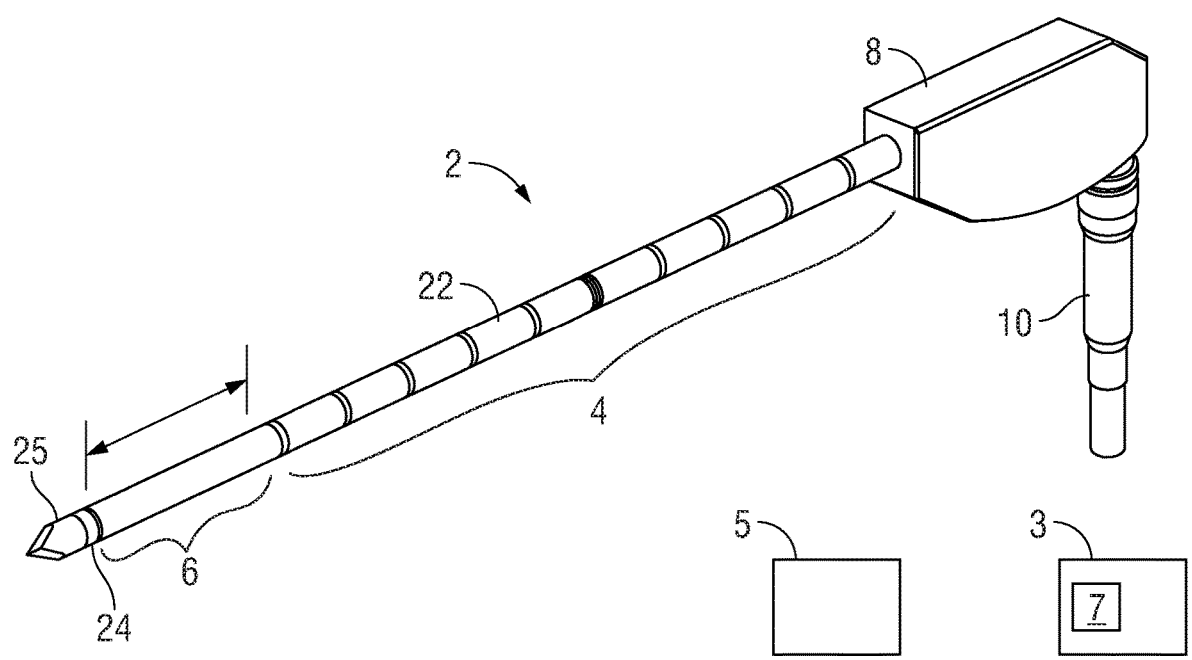
FIG. 1 is a right, perspective view of an ablation probe having a sensing configuration according to an embodiment of the present disclosure.

Turning now to FIG. 1, an ablation probe 2 including a sensor configuration 4 according to an embodiment of the present disclosure is illustrated. In accordance with the instant disclosure, sensor configuration 4 may also be utilized to serve as centimeter depth markings. Ablation probe 2 is configured to electrosurgically treat tissue utilizing electrosurgical energy having a frequency that ranges from about 2300 MHz to about 2450 MHz. In embodiments, ablation probe 2 may be configured to electrosurgically treat tissue utilizing electrosurgical energy having a frequency that is less than 2300 MHz (e.g., 915 MHz) and greater than 2450 MHz. It has been shown through empirical testing that utilizing microwave energy from about 2300 MHz to about 2450 MHz has clear advantages when compared to more traditional frequency platforms, e.g., 915 MHz. Specifically, and in accordance with the instant disclosure, ablation probe 2 utilizes microwave energy that is provided by a microwave energy source, e.g., a generator 3 (FIG. 1), and transmitted at a frequency that ranges from about 2300 MHz to about 2450 MHz to create ablation zones that have a more spherical configuration for a specified range of activation times when compared to conventional ablation probes. Moreover, this higher frequency range allows ablation probe 2 to utilize a radiating section 6 (FIG. 1) that includes a length that is relatively short when compared to radiating sections of conventional ablation probes. As can be appreciated, radiating section 6 provides enhanced focus of the microwave energy transmitted therefrom and into target tissue, which, in turn, allows the microwave energy to penetrate deeper and faster into target tissue, which, in turn, results in a desired tissue effect with shorter activation times of radiating section 6.

Continuing with reference to FIG. 1, ablation probe 2 includes a housing 8 that is formed from one or more suitable materials, e.g., plastic, metal, metal alloy, ceramic, etc. Housing 8 functions as a handle that may be grasped by a user and is configured to house one or more components of ablation probe 2. A proximal end of housing 8 operably couples to a hub 10 (FIG. 1) that couples a cable 12 to ablation probe 2 and one or more leads 14, 16 (FIG. 2) that are disposed within housing 8. Proximal end 8 also couples to in-flow and out-flow tubes 18, 20 (FIG. 2), respectively, that are coupled to a coolant source 5 (FIG. 1) configured to provide one or more suitable coolants, e.g., saline, to a shaft 22 that serves as a cooling jacket and surrounds radiating section 6.

Figure 6:
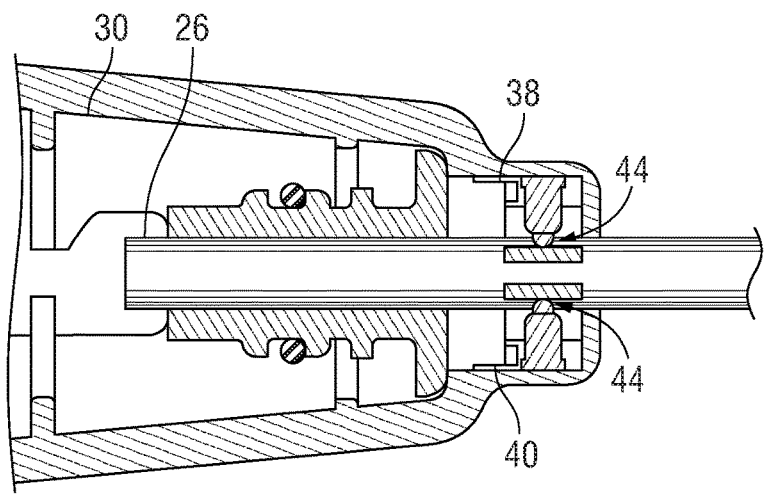
FIG. 6 is a partial, top elevated view of the ablation probe depicted in FIG. 1 with a top portion of a housing being removed and a top portion of a sensor housing removed to illustrate the sensor contacts in contact with sensor pads disposed on the shaft of the ablation probe.

Shaft 22 may be formed from any suitable material, e.g., metal, glass fiber, and extends distally from housing 8. In the illustrated embodiment, shaft 22 is formed from glass fiber Shaft 22 includes a distal end 24 (FIGS. 1 and 7A) that includes a ceramic tip 25 (FIGS. 1 and 7A) configured to pierce tissue for positioning radiating section 6 adjacent target tissue. Shaft 22 also includes a proximal end 26 that operably couples to one or more components disposed within housing 8. Specifically, proximal end 26 includes a pair of indents 28 (FIG. 7A) that are configured to couple to a pair of corresponding detents (not explicitly shown) that are provided within a hub 30 (FIGS. 2, 4 and 6).

Figure 2:
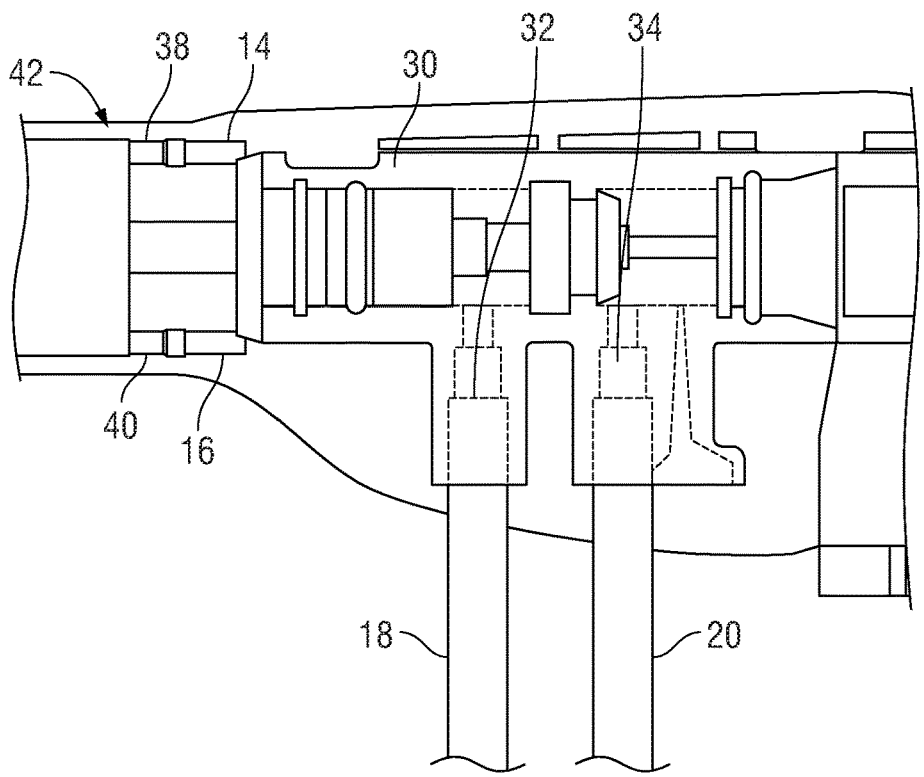
FIG. 2 is a partial, left side view of the ablation probe depicted in FIG. 1 with a left side portion of a housing being removed to illustrate a portion of a sensor assembly according to an embodiment of the present disclosure.

Hub 30 defines in-flow ports 32 and out-flow ports 34 that are configured to couple to corresponding in-flow tubes 18 and out-flow tubes 20 (FIG. 2). In-flow and out-flow ports 32, 34, respectively, communicate with one or more lumens (not explicitly shown) that extend through housing 8 and into shaft 22 forming a closed-loop path for providing coolant to radiating section 6. Hub 30 includes one or more clocking features (not explicitly shown) that align with one or more corresponding clocking features (not explicitly shown) disposed on an end cap 36 (FIG. 4) that operably couples to a distal end of hub 30. The clocking features on hub 30 and end cap 36 are configured to provide passage for leads 14, 16 so that leads 14, 16 may be coupled to a pair of sensor contacts 38, 40 (FIGS. 2-4 and 6) of a sensor assembly 42 (FIG. 2).

Continuing with reference to FIG. 2, sensor assembly 42 is operably disposed within housing 8 and includes sensor contacts 38, 40 that are configured to contact a corresponding pair of sensor contact pads 44 (see FIGS. 6-7A for example) positioned on shaft 22. Specifically, during transmission of microwave energy from radiating section 6 into target tissue, one or more electrical parameters, e.g., capacitance and/or impedance, is induced into one or more conductive traces 46 (FIGS. 7A-7B) and detected by sensor contacts 38, 40. Alternatively, a separate interrogation circuit 7 (FIG. 1) may be configured to apply a separate voltage to conductive traces 46 and measure current associated therewith to determine capacitance and/or impedance. In this embodiment, interrogation circuit 7 may be in communication with one or more modules (not shown) of generator 3 and configured to calculate capacitance and/or impedance. The interrogation frequency utilized may range from about 50 KHz to about 4 MHz.

Figure 3:
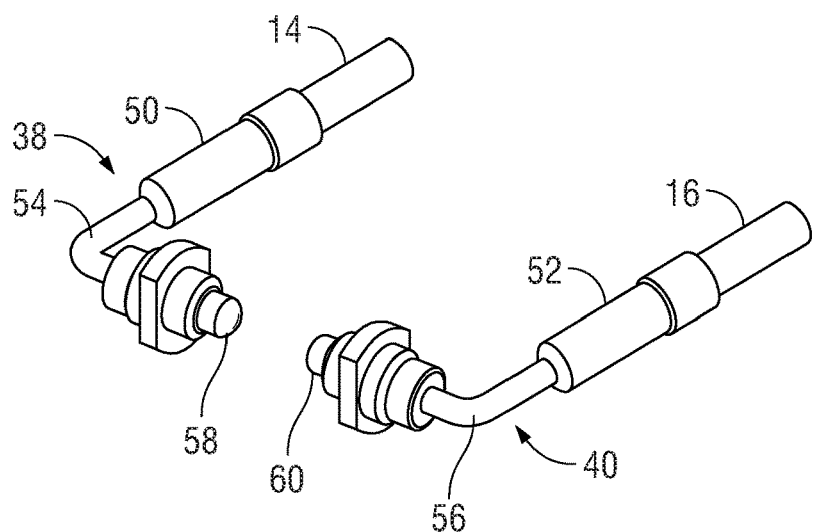
FIG. 3 is a left, perspective view illustrating a pair of sensor contacts of the sensor assembly depicted in FIG. 2.
Figure 4:
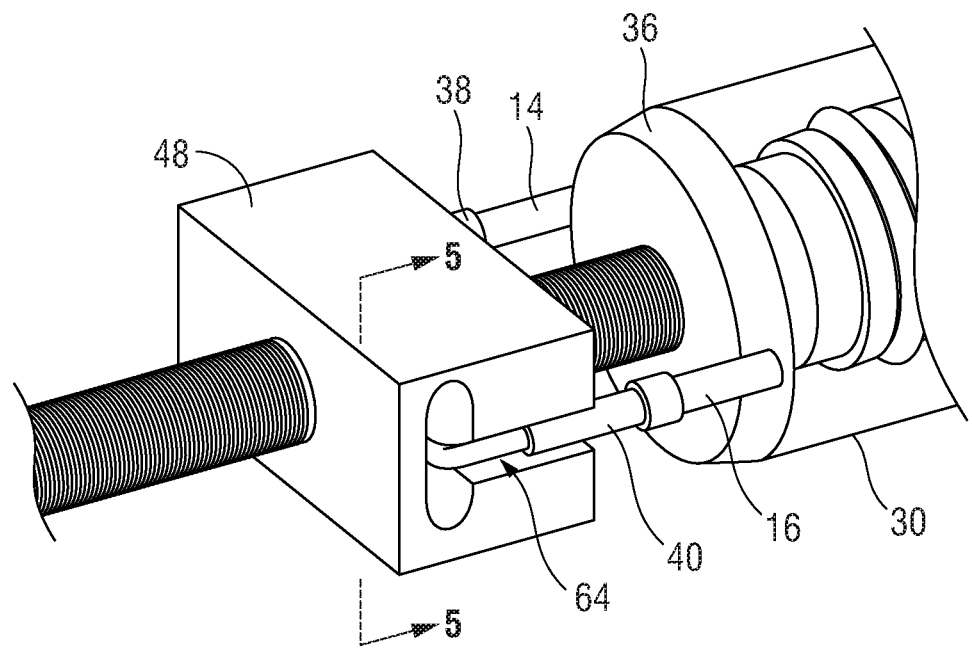
FIG. 4 is a left, perspective view illustrating the sensor assembly coupled to an end cap of the ablation probe.

Referring to FIGS. 3-4, sensor contacts 38, 40 are spaced apart a predetermined distance from one another within a sensor housing 48 that is configured to support sensor contacts 38, 40 (as best seen in FIG. 4). Proximal ends 50, 52 of sensor contacts 38, 40, respectively, are configured to couple to corresponding leads 14, 16 that extend within housing 8 (FIG. 3). Leads 14, 16 couple to the microwave energy source to provide communication between sensor contacts 38, 40 and one or more modules (not explicitly shown) of the microwave energy source.

In the illustrated embodiment, distal ends 54, 56 are offset from proximal ends 50, 52 (as best seen in FIG. 3) to facilitate contact between sensor contacts 38, 40 and sensor contact pads 44. Specifically, distal ends 54, 56 are disposed in oblique relationship with respect to respective proximal ends 50, 52 and are in substantial horizontal alignment with one another.

Figure 5:
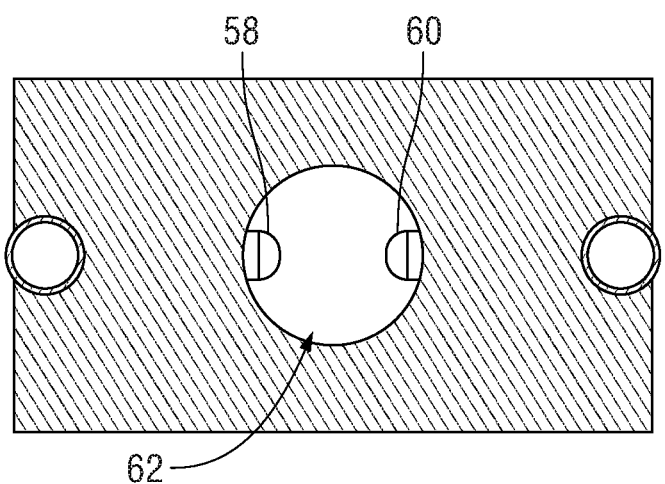
FIG. 5 is a cut-away view taken along line segment 5-5 in FIG. 4 with a shaft of the ablation probe removed.

Referring to FIG. 5, a predetermined gap is provided between the distal ends 54, 56 and may be determined during the manufacture process. More particularly, the distance of the gap between distal ends 54, 56 is smaller than an outside diameter of shaft 22; this will facilitate contact between distal ends 54, 56 and sensor contact pads 44. Specifically, each of distal ends 54, 56 includes a sensor contact surface 58, 60 (FIGS. 3 and 5) that is configured slide across a corresponding sensor contact pad 44 when shaft 22 is positioned through an aperture 62 that provides passage through sensor housing 48 (see FIGS. 4-5). In embodiments, sensor contact surfaces 58, 60 may be biased outwardly from distal ends 54, 56 and movable therein. Specifically, as shaft 22 is positioned within aperture 62 the larger diameter of shaft 22 causes sensor contact surfaces 58, 60 to translate into distal ends 54, 56. As can be appreciated, this reduces the likelihood of sensor contact surfaces 58, 60 inadvertently scrapping/or scratching off the silver ink depositions that form sensor contact pads 44 as shaft 22 is inserted through aperture 62. Additionally, distal ends 54, 56 are flexible and configured to flex when shaft 22 is positioned through aperture 62. Specifically, notched out portions 64 (one of notched portions 64 is shown in FIG. 4) are provided on sensor housing 48 and allow distal ends 54, 56 to flex or give as shaft 22 is positioned within aperture 62. The flexibility of distal ends 54, 56 may be adjusted or varied during the manufacturing process as needed.

Figure 7A:
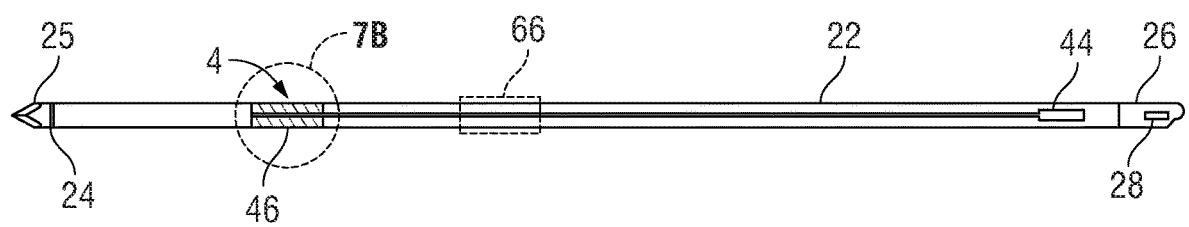
FIG. 7A is a side view of the shaft including a sensor configuration according to an embodiment of the instant disclosure.
Figure 7B:
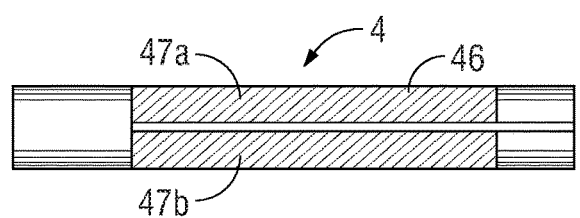
FIG. 7B is an enlarged area of detail depicted in FIG. 7A.
Figure 8A:
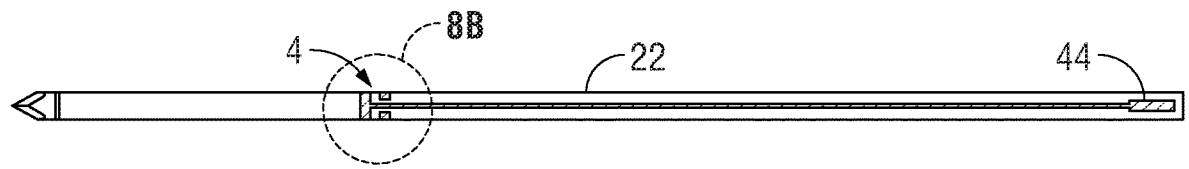
FIG. 8A is a side view of the shaft including a sensor configuration according to another embodiment of the instant disclosure.
Figure 8B:
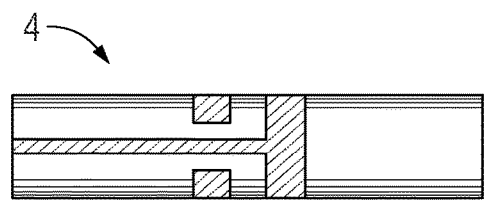
FIG. 8B is an enlarged area of detail depicted in FIG. 8A.
Figure 9A:
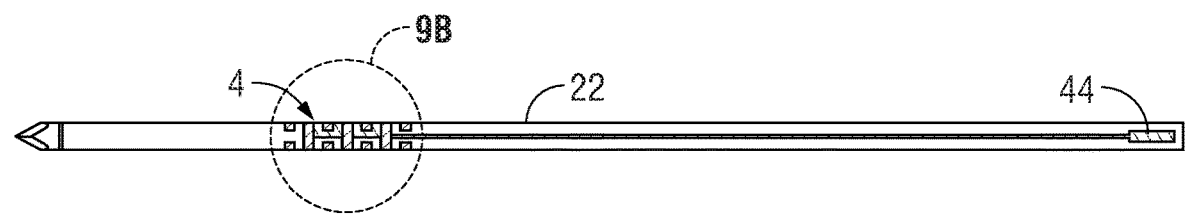
FIG. 9A is a side view of the shaft including a sensor configuration according to yet another embodiment of the instant disclosure.
Figure 9B:
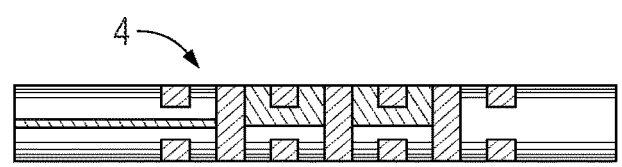
FIG. 9B is an enlarged area of detail depicted in FIG. 9A.
Figure 10A:
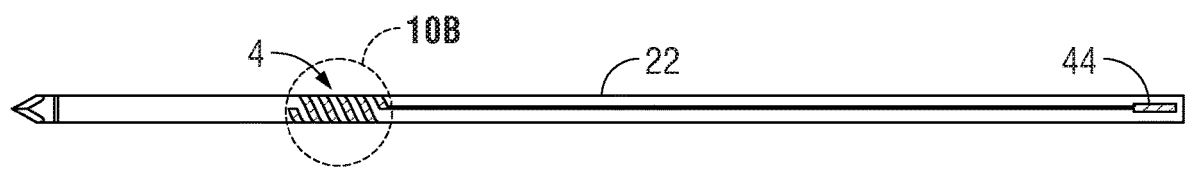
FIG. 10A is a side view of the shaft including a sensor configuration according to still another embodiment of the instant disclosure.
Figure 10B:
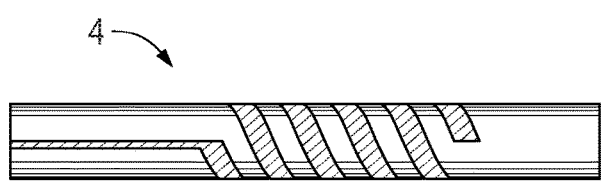
FIG. 10B is an enlarged area of detail depicted in FIG. 10A.
Figure 11:
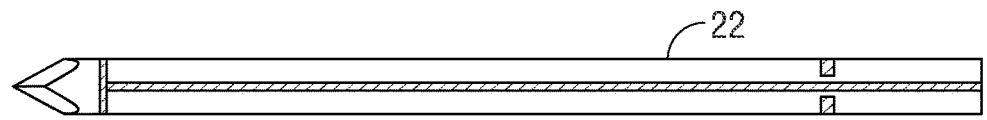
FIG. 11 is a side view of the shaft including a sensor configuration according to still yet another embodiment of the instant disclosure.
Figure 12A:
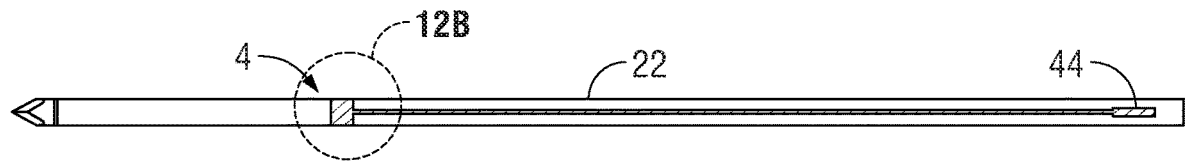
FIG. 12A is a side view of the shaft including a sensor configuration according to still yet another embodiment of the instant disclosure.
Figure 12B:
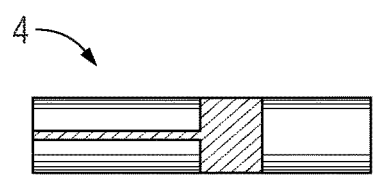
FIG. 12B is an enlarged area of detail depicted in FIG. 12A.
Figure 13A:
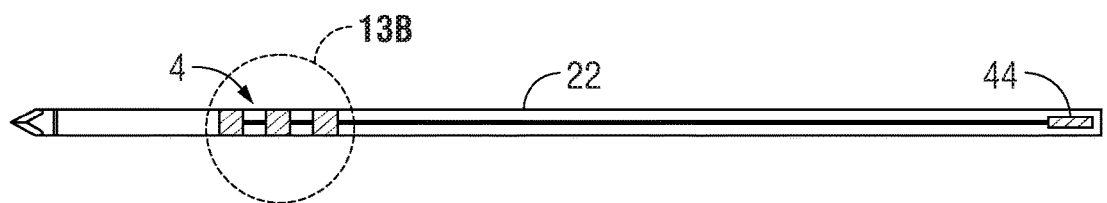
FIG. 13A is a side view of the shaft including a sensor configuration according to still yet another embodiment of the instant disclosure.
Figure 13B:
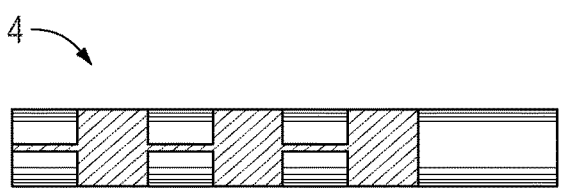
FIG. 13B is an enlarged area of detail depicted in FIG. 13A.
Figure 14A:
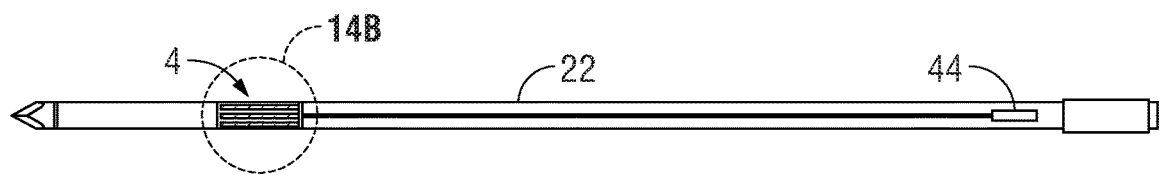
FIG. 14A is a side view of the shaft including a sensor configuration according to still yet another embodiment of the instant disclosure.
Figure 14B:
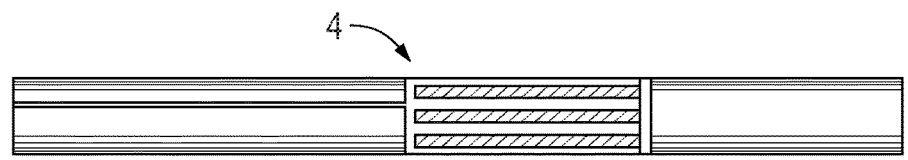
FIG. 14B is an enlarged area of detail depicted in FIG. 14A.
Figure 15A:
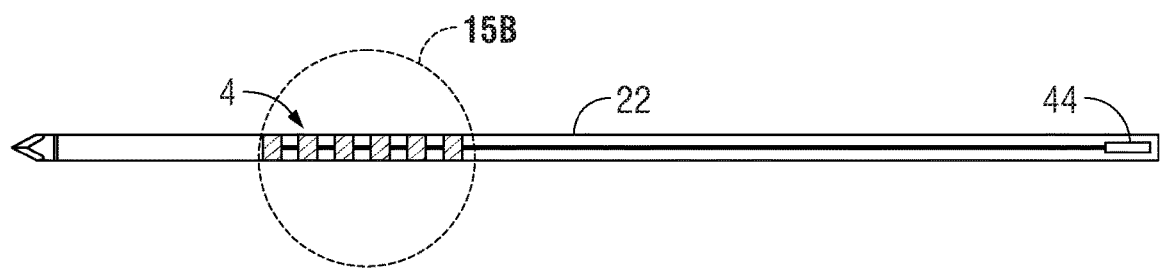
FIG. 15A is a side view of the shaft including a sensor configuration according to still yet another embodiment of the instant disclosure.
Figure 15B:
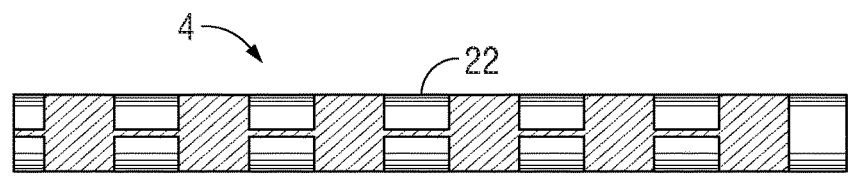
FIG. 15B is an enlarged area of detail depicted in FIG. 15A.

With reference now to FIGS. 7A-7B, an embodiment of sensor configuration 4 (sensor 4) is illustrated. In the embodiment illustrated in FIGS. 7A-7B, sensor 4 is positioned adjacent radiating section 6 and extends a predetermined length along shaft 22. In accordance with the instant disclosure, sensor 4 is defined by one or more conductive traces 46 that are formed from a silver ink deposition provided on the exterior surface of shaft 22. A silver ink deposition was utilized because of its ability to withstand EtO (Ethylene Oxide) sterilization. Other types of ink depositions including but not limited to gold, copper and nickel may also be utilized. One or more methods or processes may be utilized for depositing the silver ink onto the exterior of surface of shaft 22. For example, pad printing, laser ablation and direct write are suitable methods for depositing the silver ink onto the exterior surface of shaft 22.

In the illustrated embodiments, the silver ink deposition is utilized to form two or more conductive traces 47a, 47b (FIG. 7B) that are spaced apart a predetermined distance from one another. For example, in embodiments, the distance that conductive traces 47a, 47b are spaced apart from one another may range from about 0.010 inches to about 0.080 inches. As can be appreciated, the distance that separates conductive traces 47a, 47b may be varied or altered during the silver ink deposition process. Accordingly, in embodiments, the distance that separates conductive traces 47a, 47b may be less than 0.050 mm or greater than 0.080 mm.

Continuing with reference to FIG. 7A each of conductive traces 47a, 47 extends from distal end 24 adjacent radiating section 6 to proximal end 26 adjacent detents 28 and culminates at sensor contact pads 44 that are also formed during the aforementioned silver ink deposition process. The distance that separates conductive traces 47a, 47 and sensor contact pads 44 ranges from about 0.050 inches to about 0.100 inches. As can be appreciated, the distance that separates conductive traces 47a, 47b and sensor contact pads 44 may be varied or altered during the silver ink deposition process. Accordingly, in embodiments, the distance that separates conductive traces 47a, 47b and sensor contact pads 44 may be less than 0.001 mm or less than 0.300 mm. The important part of this feature are to have the contact pads spaced far enough apart to ensure electrical isolation from one another, but large enough pad area to ensure contact with the pogo-pin.

FIGS. 8A-15B illustrate various other configurations of sensor 4. Each of the configurations of sensor 4 shown in FIGS. 8A-15B may be formed utilizing the aforementioned materials and silver ink deposition processes. Sensors 4 illustrated in FIGS. 7A-15B may include any suitable configuration, such as, for example, two horizontal bars (FIGS. 8A-8B), two vertical bars (FIGS. 7A-7B), multi-band horizontal bars (FIGS. 9A-9B), spiral bars (FIGS. 10A-10B), or other suitable configuration (see FIGS. 11-15B for example). The specific configuration of sensor 4 utilized with ablation probe 2 will depend on a manufactures preference, a type of surgical procedure, target tissue (e.g., liver, ling, kidney, etc.), signal to noise ration parameters, etc.

A shrink wrap 66 (shown in phantom in FIG. 7A), e.g., polyester heat shrink wrap, is provided along shaft 22 to encapsulate conductive traces 47a, 47b and sensor contact pads 44. Shrink wrap 66 is utilized to maintain the structural integrity of conductive traces 47a, 47b and/or sensor contact pads 44. Moreover, shrink wrap 66 is utilized to protect a patient from silver bio-incompatibility. Further, it serves as a nonstick coating to prevent ablated tissue from sticking to sensor 4, e.g., conductive traces 47a, 47b.

In accordance with the instant disclosure, ablation probe 2 is configured to function in two modes of operation. Specifically, in a first mode of operation, e.g., a standard or manual ablation mode, sensor 4 may be configured to detect when ablation probe 2 or component associated therewith, e.g., radiating section 6, has been properly inserted, e.g., fully positioned, within target tissue and may be configured to automatically terminate power to ablation probe 2 if radiating section 6 is inadvertently or purposefully removed from target tissue. In this particular mode of operation, a clinician may position radiating section 6 of ablation probe 2 within target tissue. One or more modules associated with generator 3 may be coupled to conductive traces 47a, 47b and configured to send an interrogatory pulse thereto to determine if radiating section 6 has been properly inserted into target tissue, e.g., liver tissue. If the module(s) detects a predetermined capacitance and/or impedance induced within conductive traces 47a, 47b, a clinician may initiate the transmission of microwave energy to radiating section 6. It has been shown through empirical testing that suitable interrogation frequencies for capacitance may range from about 200 KHz to about 600 KHz. Moreover, it has been shown through empirical testing that suitable interrogation frequencies for impedance may range from about 40 KHz to about 600 KHz. In manual mode of operation, generator 3 automatically shuts off if radiating section 6 is inadvertently or purposefully removed from target tissue during transmission of microwave energy therefrom.

Moreover, in a second mode of operation, e.g., a resection mode, the generator may be configured to automatically initiate and terminate power to ablation probe 2 based on proper insertion of ablation probe 2. In this particular mode of operation, a clinician may position radiating 6 of section ablation probe 2 within target tissue. One or more modules associated with generator 3 may be coupled to conductive traces 47a, 47b and configured to send an interrogatory pulse thereto to determine if radiating section 6 has been properly inserted into target tissue, e.g., liver tissue. In resection mode, if the module(s) detects a predetermined capacitance and/or impedance induced within conductive traces 47a, 47b, generator 3 automatically initiates the transmission of microwave energy to radiating section 6. Generator 3 automatically shuts off if radiating section 6 is inadvertently or purposefully removed from target tissue during transmission of microwave energy therefrom. This particular mode of operation allows a clinician to rapidly change positions down a resection line without having to manually turn the generator on and off.

From the foregoing and with reference to the various figure drawings, those skilled in the art will appreciate that certain modifications can also be made to the present disclosure without departing from the scope of the same. For example, while the aforementioned disclosure has been described in terms of use of utilizing sensor 4 in conjunction for determining proper insertion of radiating section 6 into tissue, sensor 4 may be utilized to determine other parameters that may associated with ablation probe 2 and/or a surgical procedure. For example, sensor 4 may be configured to detect tissue type, progression of a microwave ablation procedure, completion of a microwave ablation procedure, etc. Moreover, in embodiments, sensor 4 may be utilized to detect the presence of a cooling fluid that is being circulated through ablation probe 2 and/or component associated therewith, e.g., shaft 22; this could mitigate circulation errors, e.g., a clinician forgets to circulate fluid to radiating section 6. As can be appreciated, this may increase the operative shelf life of radiating section 6 and/or ablation probe 2.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for manufacturing a microwave ablation probe comprising:
   forming a housing configured to couple to a microwave energy source;
   forming a shaft defining a longitudinal axis, the shaft having a pair of sensor contact pads and a radiating section for electrosurgically treating tissue;
   forming a pair of sensor contacts that couples to the interior of the housing; and
   coupling the shaft to the housing such that each sensor contact pad of the pair of sensor contact pads contacts a first portion of a corresponding one of the sensor contacts, the first portion of each of the pair of sensor contacts extending perpendicularly from a second portion toward the longitudinal axis defined by the shaft, the second portion of each of the pair of sensor contacts defining a longitudinal axis that extends along the longitudinal axis defined by the shaft.

2. The method according to claim 1, including forming the pair of sensor contact pads on an exterior surface of the shaft via a silver ink deposition.

3. The method according to claim 2, wherein forming the pair of sensor contact pads via the silver ink deposition includes utilizing a process selected from the group consisting of pad printing, laser ablation and direct write.

4. The method according to claim 2, wherein forming the pair of sensor contact pads via the silver ink deposition includes forming at least two depositions that are spaced-apart from one another forming at least two conductive traces that culminate at the sensor contact pads.

5. The method according to claim 1, further comprising overmolding a sensor housing to support at least a portion of the pair of sensor contacts therein.

6. The method according to claim 1, further comprising bending each sensor contact such that a distal end of each sensor contact is angled toward the other sensor contact.

7. The method according to claim 1, wherein coupling the shaft to the housing includes disposing a proximal portion of the shaft within an interior of the housing such that a distal portion of the shaft extends distally from the housing.

8. A method for manufacturing an electrosurgical device, comprising:
    coupling an elongated shaft to a housing, the elongated shaft defining a longitudinal axis and configured to electrosurgically treat tissue; and
    coupling a sensor contact pad disposed on the elongated shaft to a first portion of a sensor contact disposed within the housing, the first portion of the sensor contact extending perpendicularly from a second portion of the sensor contact toward the longitudinal axis defined by the elongated shaft.

9. The method according to claim 8, wherein the second portion of the sensor contact defines a longitudinal axis that extends along the longitudinal axis of the elongated shaft.

10. The method according to claim 8, further comprising coupling a pair of sensor contact pads disposed on the elongated shaft with a first portion of each of a pair of sensor contacts disposed within the housing, the first portion of each of the pair of sensor contacts extending perpendicularly from a second portion toward the longitudinal axis defined by the elongated shaft.

11. The method according to claim 8, wherein coupling the elongated shaft to the housing includes disposing a proximal portion of the elongated shaft within an interior of the housing such that a distal portion of the elongated shaft extends distally from the housing.

12. The method according to claim 8, wherein coupling the elongated shaft to the housing includes coupling the sensor contact pad with a sensor contact surface disposed on a distal end portion of the first portion of the sensor contact.

13. A method for manufacturing an electrosurgical device, comprising:
    disposing a sensor contact within a housing, the sensor contact having a first portion extending perpendicularly from a second portion; and
    coupling an elongated shaft defining a longitudinal axis to the housing to couple a sensor contact pad disposed on the elongated shaft with the first portion of the sensor contact, the elongated shaft configured to electrosurgically treat tissue.

14. The method according to claim 13, wherein coupling the elongated shaft to the housing includes positioning the elongated shaft such that a longitudinal axis defined by the second portion of the sensor contact extends along the longitudinal axis defined by the elongated shaft.

15. The method according to claim 13, wherein the first portion of the sensor contact extends perpendicularly from the second portion of the sensor contact toward the longitudinal axis defined by the elongated shaft upon coupling the elongated shaft to the housing.

16. The method according to claim 13, wherein coupling the elongated shaft to the housing includes coupling the sensor contact pad with a sensor contact surface disposed on a distal end portion of the first portion of the sensor contact.

17. The method according to claim 13, wherein coupling the elongated shaft to the housing includes disposing a proximal portion of the elongated shaft within the housing such that a distal portion of the elongated shaft extends distally from the housing.

\* \* \* \* \*